US011000669B2

(12) United States Patent
Derungs

(10) Patent No.: US 11,000,669 B2
(45) Date of Patent: *May 11, 2021

(54) METHOD OF VIRTUAL REALITY SYSTEM AND IMPLEMENTING SUCH METHOD

(71) Applicant: Louis Derungs, Chigny (CH)

(72) Inventor: Louis Derungs, Chigny (CH)

(73) Assignee: MINDMAZE HOLDING SA, Lausanne (CH)

(*) Notice: Subject to any disclaimer, the term of this patent is extended or adjusted under 35 U.S.C. 154(b) by 0 days.

This patent is subject to a terminal disclaimer.

(21) Appl. No.: 16/205,675

(22) Filed: Nov. 30, 2018

(65) Prior Publication Data

US 2019/0374741 A1 Dec. 12, 2019

Related U.S. Application Data

(63) Continuation-in-part of application No. 15/347,544, filed on Nov. 9, 2016, now Pat. No. 10,175,935.

(30) Foreign Application Priority Data

Oct. 8, 2016 (CH) ................ CH 01031/16

(51) Int. Cl.
*A61B 5/024* (2006.01)
*G02B 27/01* (2006.01)
(Continued)

(52) U.S. Cl.
CPC ........... *A61M 21/02* (2013.01); *A61B 5/0205* (2013.01); *A61B 5/02405* (2013.01);
(Continued)

(58) Field of Classification Search
CPC .. A61B 5/0205; A61B 5/02405; A61N 21/02; A61M 2021/0027; G02B 27/017; G02B 2027/0178
(Continued)

(56) References Cited

U.S. PATENT DOCUMENTS 10,175,935 B2 * 1/2019 Derungs ................ A61B 5/02
2014/0171729 A1 * 6/2014 Bourne ................ A61M 21/00
600/27

(Continued)

*Primary Examiner* — Hemant S Patel
(74) *Attorney, Agent, or Firm* — Graeser Associates International Inc; Dvorak Graeser

(57) ABSTRACT

Virtual reality method intended to be implemented in a virtual reality system, the method including the production of a stimulus in the system during a period of stimulation, the stimulus including: a projection of an image sequence; a production of a first sound signal including a soundtrack linked to the progress of the image sequence; a production of a second sound signal having a first frequency and a third sound signal having a second frequency, the second sound signal being audible from one ear and the third sound signal being audible from the other ear of the user; a production of a fourth sound signal including a spoken presentation; during an initial portion of said predetermined period, the stimulus further including an induction signal; and during a final portion of said predetermined period, the intensity of the sound signals decreasing in intensity until a zero intensity, and the image sequence decreasing in intensity until a zero intensity.

20 Claims, 7 Drawing Sheets

(51) Int. Cl.
  *A61B 5/0205* (2006.01)
  *A61M 21/02* (2006.01)
  *A61M 21/00* (2006.01)

(52) U.S. Cl.
  CPC ... *G02B 27/017* (2013.01); *A61M 2021/0027* (2013.01); *G02B 2027/0178* (2013.01)

(58) Field of Classification Search
  USPC .......................................................... 700/94
  See application file for complete search history.

(56) References Cited

U.S. PATENT DOCUMENTS

2014/0350706 A1\* 11/2014 Morishima ............ G10K 15/04
  700/94
2016/0235323 A1\* 8/2016 Tadi ..................... A61B 5/7285

\* cited by examiner

METHOD OF VIRTUAL REALITY SYSTEM AND IMPLEMENTING SUCH METHOD

TECHNICAL FIELD

The present invention relates to a virtual reality method and a system implementing such a method.

BACKGROUND ART

The use is known of a device for supporting a user or a patient so as to lead them into a deep altered state of consciousness until a deep state of hypnosis.

U.S. Pat. No. 8,517,912 describes a medical hypnosis device for controlling a hypnosis experience in a patient. The device includes output means for providing a first type of content that may be a virtual reality type of representation.

US Patent Application No. 2006247489 describes a device and a method of relaxation and meditation by hypnosis in a virtual environment. The device includes an audiovisual headset connectable to a portable DVD player for playing movies from DVD media so as to lead the user into a state of relaxation until a deep state of hypnosis. The device may include a 2D or 3D monitor.

US Patent Application No. 2015174362 describes an apparatus including a virtual reality module and a method for inducing a state of hypnosis. The apparatus includes a head-mounted display for delivering a virtual reality audiovisual signal to the patient and collecting their biological signals.

BRIEF SUMMARY OF THE INVENTION

The present invention relates, in at least some embodiments, to a virtual reality method intended to be implemented in a virtual reality system, the method including the production of a stimulus in the system during a period of stimulation, the stimulus including:
  a projection of an image sequence;
  a production of a first sound signal including a soundtrack linked to the progress of the image sequence;
  a production of a second sound signal having a first frequency and a third sound signal having a second frequency, the second sound signal being audible from one ear and the third sound signal being audible from the other ear of the user;
  a production of a fourth sound signal including a spoken presentation;
  during an initial portion of said predetermined period, the stimulus further including an induction signal; and
  during a final portion of said predetermined period, the intensity of the sound signals decreasing in intensity until a zero intensity, and the image sequence decreasing in intensity until a zero intensity.

The present invention also relates to a virtual reality system adapted to the virtual reality method and to a computer medium including portions of code of an application program intended to be executed by the virtual reality system so as to implement the method.

These solutions notably offer the advantage compared with the prior art of providing more effective relaxation and meditation techniques compared with the prior art.

BRIEF DESCRIPTION OF THE FIGURES

Examples of implementation of the invention are set out in the description illustrated by the appended figures in which.

EXAMPLE(S) OF EMBODIMENTS

Figure 1:
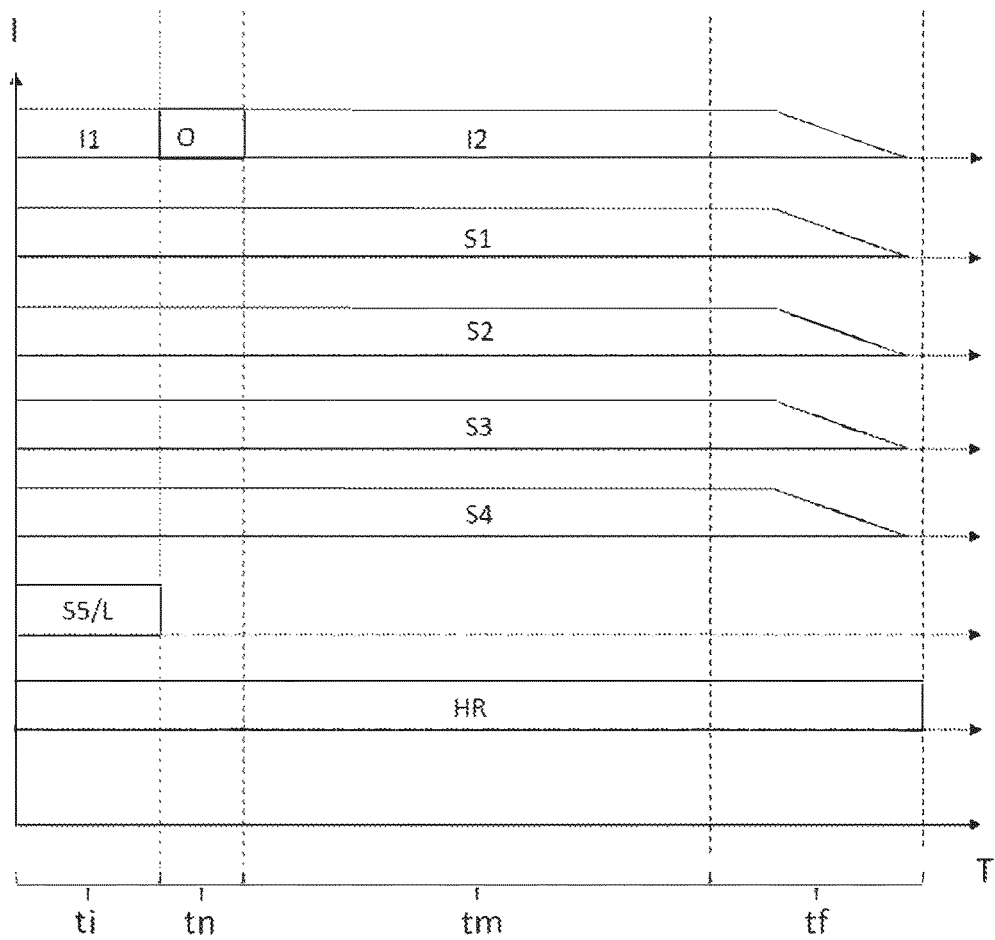
FIG. 1 schematically illustrates a virtual reality system including a virtual reality device and a display device, according to one embodiment.

FIG. 1 represents a virtual reality method intended to be implemented in a virtual reality system, according to one embodiment. The method includes the production of a stimulus during a period of stimulation. The stimulus may include a projection of an image sequence I1. The stimulus may also include the production of the first sound signal S1 including a soundtrack linked to the progress of the image sequence I1. The stimulus may also include the production of the second sound signal S2 having the first frequency f1 and of the third sound signal S3 having the second frequency f2. The second sound signal is audible from one ear of the user and the third sound signal being audible from the other ear of the user. The stimulus may also include the production of a fourth sound signal S4 including a spoken presentation.

During an initial portion ti of the period of stimulation, the stimulus further includes an induction signal S5. During a final portion tf of the period of stimulation, the intensity of the sound signals S1-S4 decrease in intensity until a zero intensity, and the intensity of the image sequence I1 decreases until reaching a zero intensity.

The intensity for sound and image sequences may relate to the level of sound or brightness, respectively. The sound signals start with a certain initial volume, which then decreases or becomes lower progressively, until at the end the sound may be barely audible or inaudible. Preferably a similar process is followed for brightness and precision of the image. For example, if the image is quite bright and there are some noises provided for the sound signals, the volume and perception of the noises will decrease slowly until reaching complete silence, and in the same time the image brightness and precision will also decrease. The image will preferably become more and more blurry up to reaching a completely black environment, accompanied by complete silence.

According to one implementation, the first frequency f1 of the second sound signal S2 differs from the second frequency f2 of the third sound signal S3. For example, the difference between the first and the second frequency f1, f2 may be constant over one portion or the whole of the period of stimulation. In particular, the difference between the first and the second frequency f1, f2 is between 5 Hz and 12 Hz.

According to one implementation, the first and the second frequency f1, f2 vary during the portion or the whole of the stimulation period, so that the difference between the first and the second frequency f1, f2 remains constant. Typically, the first and the second frequencies f1, f2 are between 20 Hz and 600 Hz.

In one embodiment, the fourth sound signal S4 includes a spoken presentation forming a discourse of a hypnotic character. The fourth sound signal S4 may be prerecorded or recited by an operator through a device in communication with the virtual reality system 1. The spoken presentation may be used to influence and lead the user 10 toward a state of relaxation and meditation.

A discourse that is of hypnotic character is a discourse that is oriented towards installing some sort of plasticity in cognitive schematics by loading up the rational mind in order to have access to more deep processes. It is built around several techniques and follows some sort of methodology. For example as described herein, the discourse may be provided according to the described the time sequences. In a nutshell, it is about orienting the mind inside and outside, towards interoceptive signals but also external stimuli, using the representations of the patient in order to restructure cognitive schematics orienting the understanding of the world. Each user creates a perception of external reality, based at least in part upon the user's internal reality. The hypnotic discourse enables reshaping the schematics that the user employs in order to build the user's reality, thoughts, memory, and sense of self.

Figure 2:
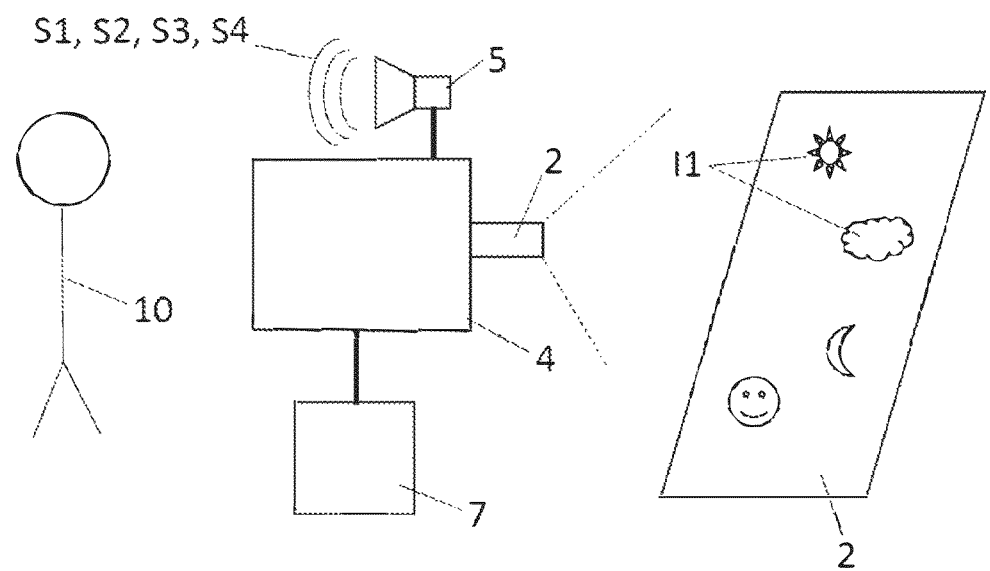
FIG. 2 represents a method intended to be implemented in the virtual reality system, according to one embodiment.

FIG. 2 schematically illustrates a virtual reality system 1 adapted to the implementation of the method, according to one embodiment. The system 1 includes a virtual reality module 4 comprising a display device 2 configured for projecting an image sequence I1 in the visual field of a user 10. The virtual reality module 4 also includes an audio playback device 5 configured for producing the first sound signal S1, the second sound signal S2 having the first frequency f1 and audible from one ear of the user, the third sound signal S3 having the second frequency f2 and audible from the other ear of the user, and the fourth sound signal S4 including a spoken presentation. The system 1 also includes a control unit 7 configured for controlling the virtual reality module 4. The projection of the image sequence I1 with the soundtrack S1 by means of the display device 2 and the audio playback device 5 of the virtual reality system 1 may be used to simulate the presence of the user 10 in the real or imaginary environment projected by the image sequence I1 (e.g. a movie). The virtual reality system 1 may allow a playback of movies with sound or image sequences with sound and customized, notably at the request of the user 10.

The virtual reality system 1 may be adapted so that the second sound signal S2 and the third sound signal S3 are respectively only audible by one or the other ear of the user 10.

The projection of the image sequence I1 implemented by the virtual reality system 1 allows the user to interact spatially with the projected environment, e.g. by changing the angle of view of the environment by changing their posture, e.g. by turning their head or torso.

Figure 3:
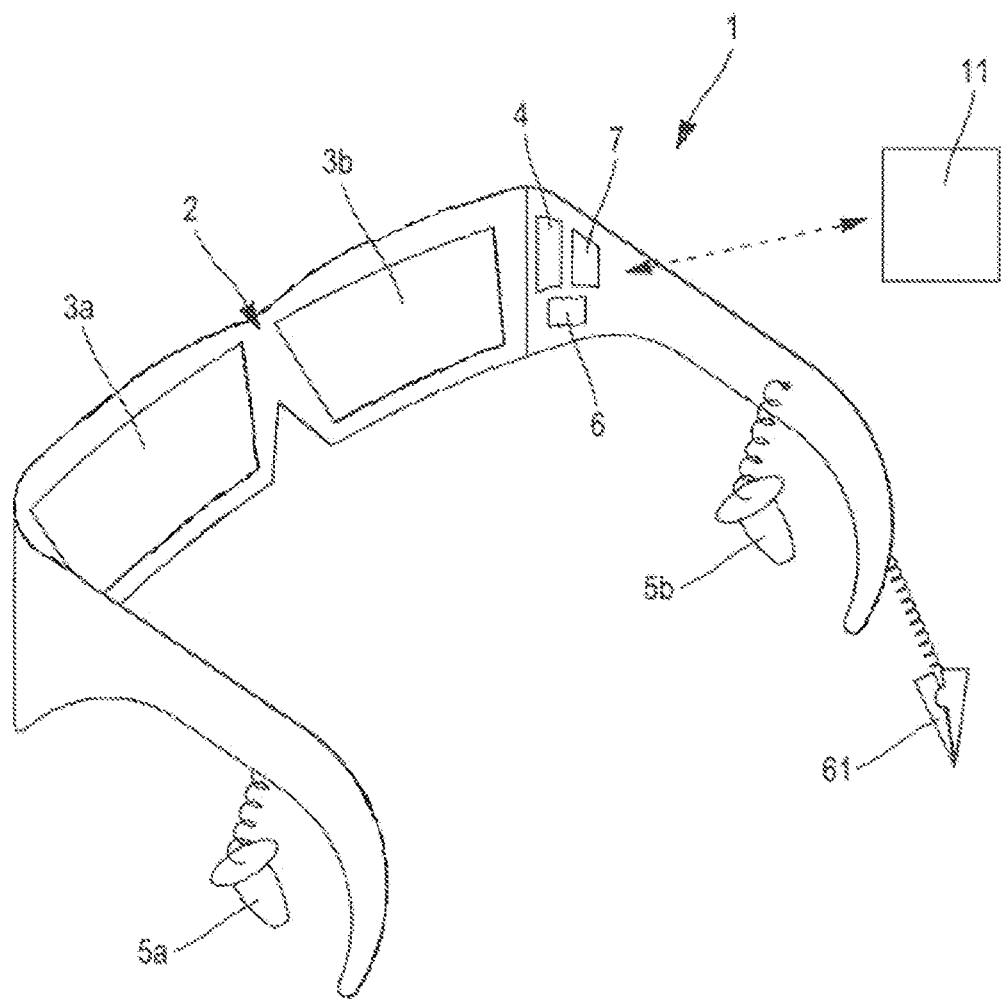
FIG. 3 depicts the virtual reality system according to a particular embodiment.

FIG. 3 depicts the virtual reality system 1 according to a particular embodiment in which the system 1 takes the form of eyeglasses 1 worn by the user. The display device 2 includes two display screens 3a, 3b corresponding to the lenses of the eyeglasses so that each display screen 3a, 3b is in the visual field of one of the two eyes of the user 10, when the system 1 is worn by the user 10.

According to one implementation, the audio playback device 5 includes two transducers 5a, 5b, e.g. in the form of earpieces. Each transducer 5a, 5b allows the production of the second sound signal S2 and the third sound signal S3 in each of the ears of the user 10.

In one embodiment, during a median portion tm subsequent to the initial portion ti and preceding the final portion tf, the production of the image sequence I1 allows an interaction of the user with the image sequence I1. For example, characteristics of the image sequence I1, notably the light intensity, are changed by the interaction of the user 10.

The median portion tm may therefore allow the user to interact with the image sequence I1 and/or with the fourth sound signal S4.

For example, the image sequence I1 may include one or a plurality of virtual objects that appear and/or disappear as a result of the interaction of the user 10. The interaction of the user 10 may include includes a movement of the user in relation to the object. Alternatively, the movement of the user 10 may include directing the gaze of their eyes and/or an orientation of their head (e.g. in the direction of an object or objects) for a predetermined period of time.

The display device 2 may be arranged so that the image sequence I1 produced allows an interaction of the user 10. For this purpose, the display device 2 may be configured for changing the characteristics of the image sequence I1, e.g. the light intensity of the images, as a result of an interaction of the user 10.

Advantageously, the display device 2 is configured so as to cause one or a plurality of virtual objects included in the image sequence I1 to appear and/or disappear, as a result of an interaction of the user 10. The appearance and/or the disappearance of the virtual object or objects may occur in a predefined period of time after the interaction, so as to induce a beneficial state of mind in the user.

The user 10 may be led, by means of the spoken presentation S4, to indicate one or more virtual objects with which they interact. The spoken presentation S4 may also be used to identify the virtual object or objects with which the user 10 will interact. The interaction may also be performed orally by the user 10 only or in addition to the movement of the user 10.

Figure 4:
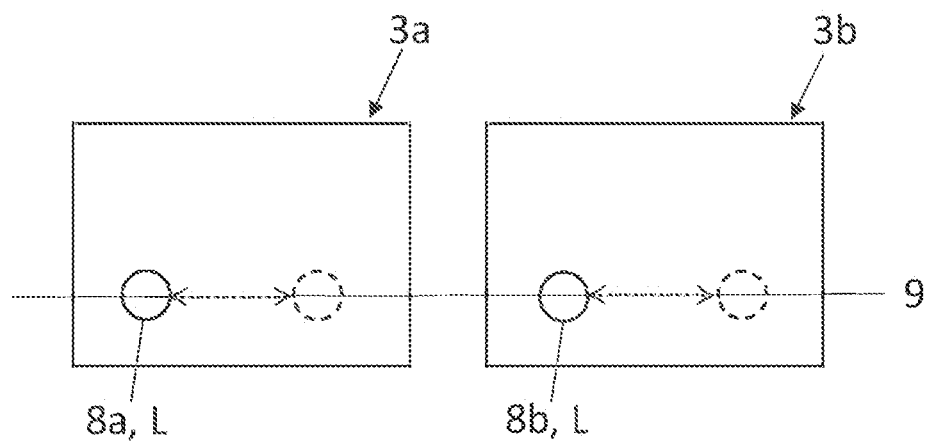
FIG. 4 depicts a display device, according to one embodiment.

According to one implementation, during the initial portion ti of the period of stimulation, the induction signal S5 includes a projection of a light signal L superimposed on the image sequence I1 (see FIG. 4). The light signal L may be displaced in a random or predetermined movement between a first and a second area of the image sequence I1. In a variant, the light signal L is displaced rhythmically in a to-and-fro movement between a first and a second area of the image sequence I1. The purpose of the induction signal S5 is to facilitate the transition of the user to a state of relaxation and meditation, or even hypnosis.

During the initial period ti, the projection of the image sequence I1 with the soundtrack S1 may take on a scenic character, favoring relaxation in the user 10. The image sequence I1 may thus allow the user 10 to view a succession of backgrounds. In addition, one or more light patterns (such as a dot or other) may be superimposed on the image sequence. Each light pattern may have a distinct and uniform color. These images, possibly with the light pattern or patterns, may be used, for example, to implement a calm and relaxing scene and/or chromotherapy techniques.

At the end of the initial period ti, the production of the induction signal S5 ceases.

FIG. 4 illustrates the display device 2 configured for simultaneously displaying a first virtual object 8a (or a light signal L) via the first display screen 3a and a second virtual object 8b (or another light signal L) via a second display 3b.

Such an arrangement may be used to generate a stereoscopic vision effect, i.e. to reproduce a perception of a relief of the virtual object 8a, 8b from two plane images illustrated by the two screens 3a, 3b. These virtual objects may be superimposed on the image sequence I1.

The first virtual object 8a may be displaced rhythmically in a to-and-fro movement between a first and a second area of the first screen 3a. In a similar way, the second virtual object 8b may be displaced rhythmically in a to-and-fro movement between a first and a second area of the second screen 3b.

In the example in FIG. 4, the first virtual object 8a and the second virtual object 8b are displaced along a line of displacement 9 virtually linking the first screen 3a and the second screen 3b so as to displace the objects 8a, 8b between a right peripheral portion and a left peripheral portion of the field of vision of each eye. Such a configuration may be used, for example, to implement EMDR (eye movement desensitization and reprocessing) type implementation protocols developed by Shapiro and others (see for example "The Role of Eye Movement Desensitization and Reprocessing (EMDR) Therapy in Medicine: Addressing the Psychological and Physical Symptoms Stemming from Adverse Life Experiences"; Perm J. 2014 Winter; 18(1): 71-7).

Advantageously the display device 2 may be configured for dynamically varying the angle of the line of displacement 9 (with respect to the geometric arrangement of the screens 3a, 3b) in response to the lateral inclination of the system 1, when it is worn by the user 10. The line of displacement 9 may thus be maintained substantially parallel to the horizontal (i.e. perpendicular to the direction of gravity).

According to another implementation, the induction signal includes a production of a fifth sound signal S5. The fifth sound signal S5 may be displaced in a random or predetermined movement. In a variant, the fifth sound signal S5 is displaced in a to-and-fro movement between a first and a second area in the space surrounding the user.

According to one implementation, the audio playback device 5 may be configured in such a way that the induction signal S5 includes a two-channel sound being rhythmically displaced in a to-and-fro movement between a first and a second area of the space surrounding the user 10. In a preferred manner, the virtual sound source S5 may be displaced along a line virtually connecting the first and the second transducer 5a, 5b (see FIG. 3). This last configuration may be used to implement EMDR type implementation protocols developed by Shapiro.

In particular, the virtual reality system 1 is adapted to implementing a virtual reality method that requires the user 10 to perform a sequence of eye movements, this in combination with sound signals and/or predetermined image sequences which may produce scenes or other visual environments.

In one embodiment, the period of stimulation includes a dark portion tn subsequent to the initial portion ti and preceding the median portion tm, in which the image sequence consists of a total darkness O. During the dark period tn, the image sequence O simulates an environment of total darkness, e.g. by a series of dark images or by a reduction in the intensity of the images until a zero intensity or one perceived as zero. The dark period to may be used to strengthen and verify the state of relaxation and meditation in the user 10.

In yet another embodiment, the virtual reality system 1 includes at least one sensor module 6 configured for measuring a vital parameter HR (biofeedback) of the user 10. For example, the sensor module 6 may include a sensor for providing a cardiovascular signal, that may be used, for example, to determine the cardiac coherence of the user 10. Such a sensor may include an optical device such as a photoplethysmographic sensor or an ECG or ICG (impedance cardiography) sensor. FIG. 3 illustrates a photoplethysmographic sensor module taking the form of an ear-clip 61.

The control unit 7 may be configured for controlling the sensor 6 and possibly collecting and analyzing the cardiovascular signal provided by the sensor 6, e.g. so as to determine a cardiac coherence as well as a cardiac coherence threshold.

According to one implementation, the method includes a step of determining the cardiac coherence of the user 10 with the aid of the cardiovascular signal provided by the sensor module 6, during the median portion tm. The method may further include a step of returning to the initial portion ti of the period of stimulation in which the induction signal S5 is generated in order to put the user back into the desired state (e.g. in the event of a state of relaxation that is insufficient or lacking), when the determined cardiac coherence is below the cardiac coherence threshold. The initial period ti may be extended or repeated so as to induce a sufficient state of relaxation and meditation of the user.

The control unit 7 may include a transmission module (not represented) arranged for allowing data collected by the control unit 7 to be transmitted to an external module 11. The external module 11 may be configured for processing and/or displaying and/or storing the collected data. The external module 11 may also be arranged for receiving commands and/or images or image sequences intended to be generated by the display device 2 and/or to receive commands and/or sounds intended to be generated the audio playback device 5.

Advantageously, the control unit 7 may be configured for receiving voice messages from a third party so as to play them back through the audio playback device 5.

In particular, the control unit 7 may be configured for generating a database of image sequences and accessing the database so as to allow the user to download the new visual content in order to be played back with the system 1.

Figure 6:
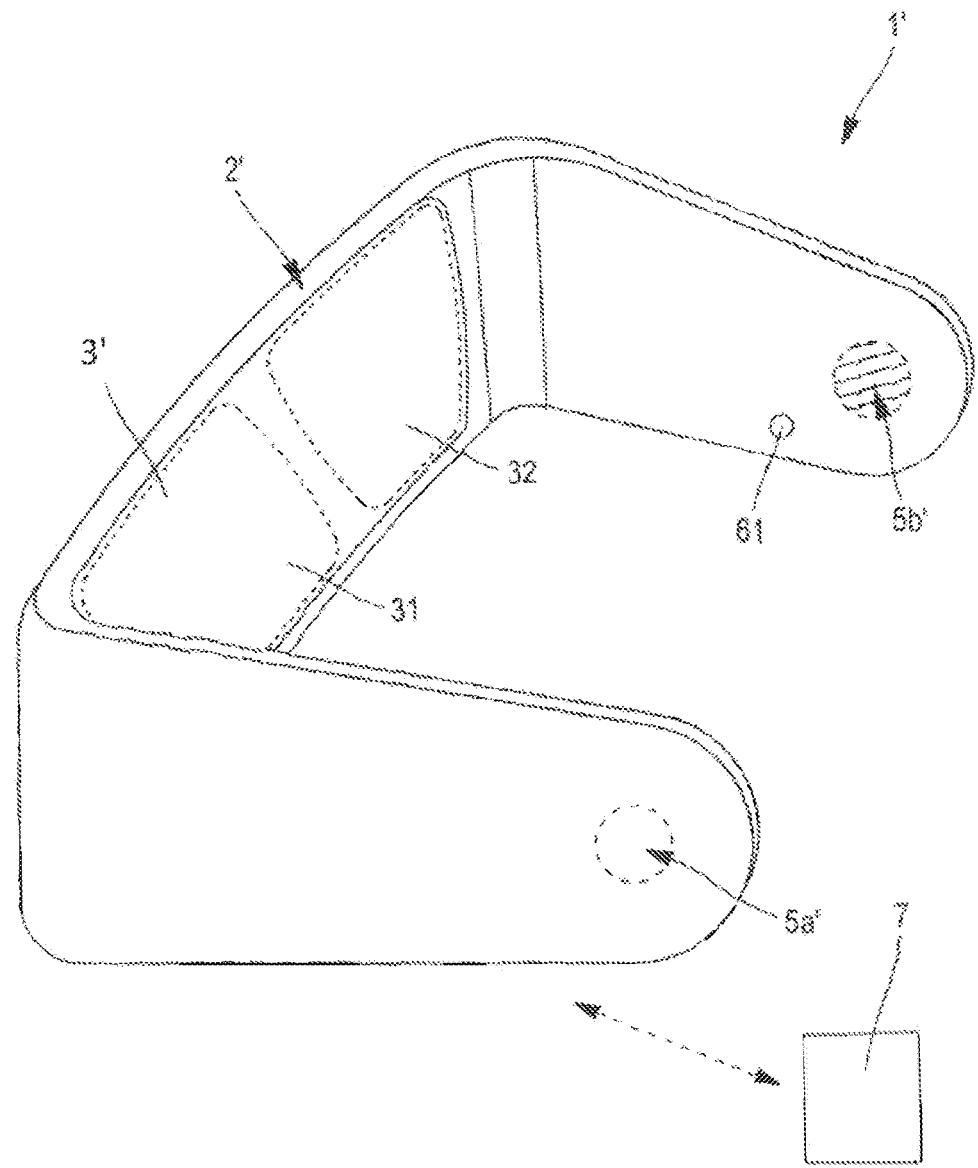
FIG. 6 depicts a variant embodiment of the virtual reality system.

FIG. 6 illustrates a variant embodiment of the virtual reality system 1. Here, the portable system 1 takes the form of a helmet-mounted display (sometimes also called a head-mounted display, immersive headset, virtual reality helmet, helmet-display or HMD helmet). This variant of the system 1 takes on the technical characteristics of the system 1 in FIG. 3. However, the display device 2 includes a single display screen 3 covering the fields of vision of both eyes of the user. A first portion 31 of the display screen 3 is positioned in the visual field of the first eye of the user, and a second portion 32 of the screen is positioned in the visual field of the second eye of the user, when the latter is wearing the system 1.

The virtual reality module 4 may be configured for displaying the first virtual object 8a and/or the second virtual object 8b via the same display screen 3. Advantageously, the virtual reality module 4 is configured for displaying the first virtual object 8a being displaced in the first portion 31 of the screen 3 and simultaneously the second object 8b being displaced in the second portion 32 of the screen 3 so as to generate a stereoscopic vision effect.

In particular, the virtual reality module 4 may be configured for displaying the first virtual object 8a being displaced rhythmically in a to-and-fro movement between a first and a second area of the first portion 31 of screen 3. The virtual reality module 4 may also be configured for displaying the second virtual object 8b being displaced rhythmically in a to-and-fro movement between a first and a second area of the second portion 32 of screen 3.

The display device 2 is arranged so that each portion of the screen 3a, 3b, 31, 32 is positioned only in one of the two fields of vision of the eyes of the user.

Figure 5:
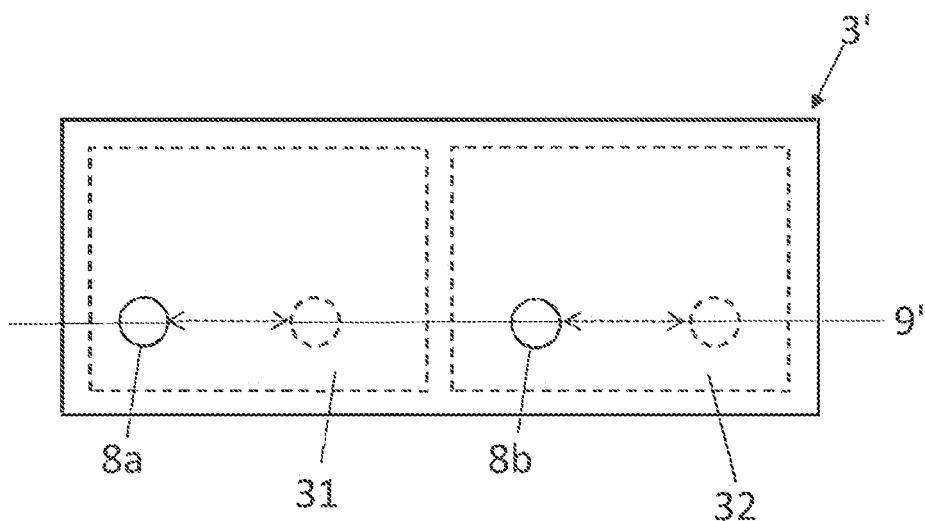
FIG. 5 illustrates an example of a display device, according to another embodiment.

FIG. 5 illustrates an example in which the display device 2 is configured so that the first virtual object 8a and the second virtual object 8b are displaced along a line of displacement 9 virtually linking the two lateral edges of the display screen 3. The virtual reality module may thus be used to implement EMDR type implementation protocols developed by Shapiro.

Advantageously the virtual reality module may be configured for dynamically varying the angle of the line of displacement 9 (with respect to the lateral edges of the display screen 3) in response to the lateral inclination of the system 1, when it is worn by the user 10. The line of displacement 9 may thus be maintained substantially parallel to the horizontal (i.e. perpendicular to the direction of gravity).

The system 1 according to the variant in FIG. 6 allows an integration of the first and second transducer 5a, 5b of the stereophonic audio playback device. The transducers 5a, 5b may thus take the form of speakers. The system 1 allows an easy integration of the sensor module 6.

According to an implementation illustrated in FIGS. 1 and 6, the control unit 7 is remote from the display device 2. The whole or a part of the virtual reality module 4 may also be remote from the display device 2. The control unit 7 (possibly also the whole or a part of the virtual reality module 4) and the sensor module 6 communicate with one another with the aid of a wireless communication protocol. In a variant, the control unit 7 and possibly also the whole or a part of the virtual reality module 4 are included in a portable apparatus such as a smartphone, a tablet, etc.

The method may include an initial step of collecting information via the virtual reality system 1. This information may be collected through a virtual questionnaire so as to allow a calibration of the various steps of the method (intensity of the sound signals S1-S5 and images I1) as well as the setting of its periods (ti, tn, tm, tf). The virtual reality system 1 may include vocal means, such as a microphone, or optical means (camera) or any other appropriate means for collecting information.

The method may be adapted to sports preparation, increasing the physical performance of an athlete, personal development, relaxation, mediation, desensitization to smoking or unhealthy eating habits, as well as preparation for dental and orthopedic operations of short duration, replacing general convenience anesthesias and installing a virtual gastric ring.

In particular, the method may be adapted to hypnosis, e.g. a combination of hypnosis and an EMDR (Eye Movement Desensitization and Reprocessing) and/or EFT (Emotional Freedom Technique) type technique.

The present invention also relates to a computer medium including portions of code of an application program intended to be executed by the control unit 7 so as to implement the method described here.

Figure 7:
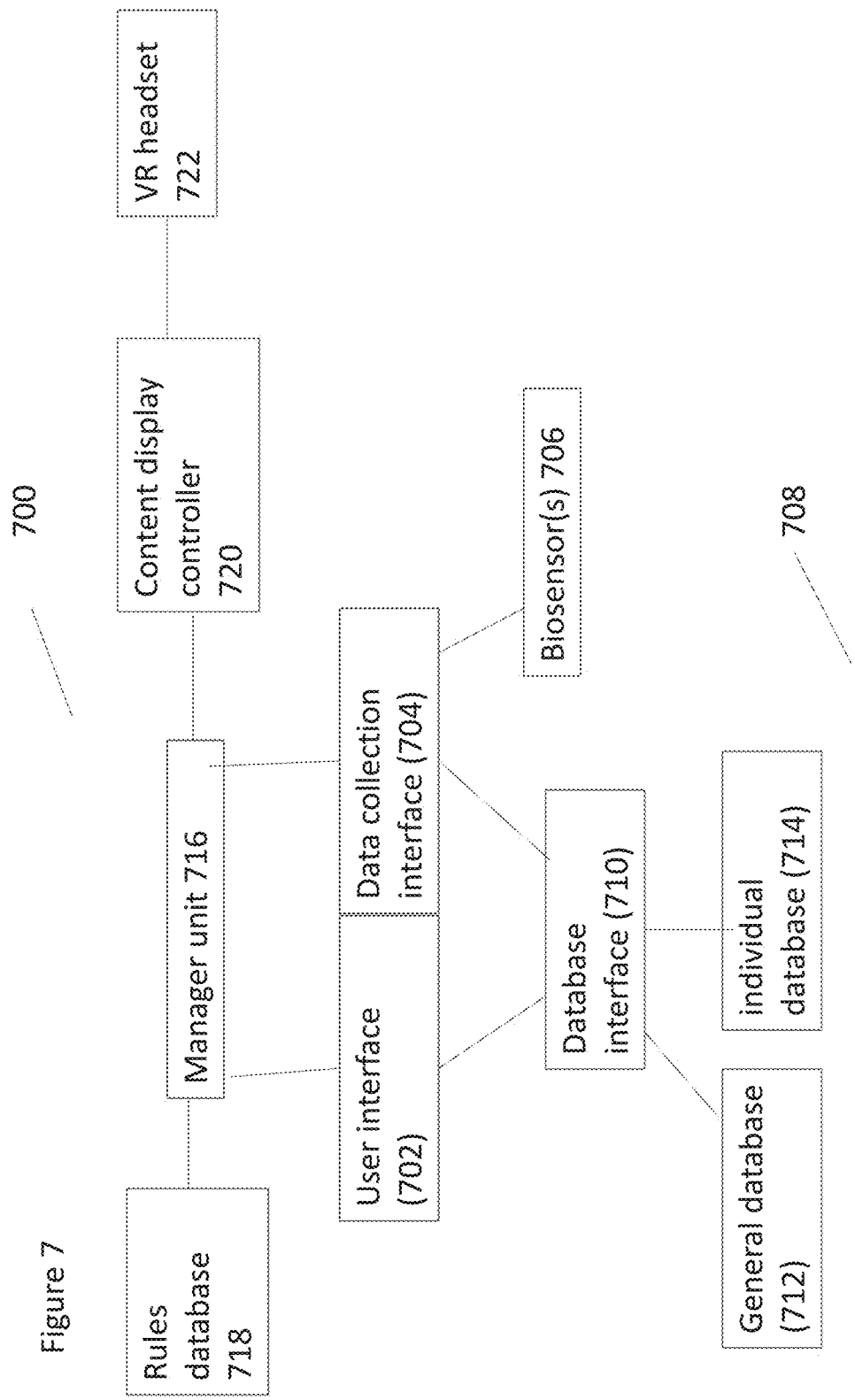
FIG. 7 shows a non-limiting exemplary implementation of a control unit, for example with the use of any system or method as described herein.

FIG. 7 shows a non-limiting exemplary implementation of a control unit, for example with the use of any system or method as described herein.

As shown, a control unit 700 collects data from the user or from a database in order to shape the content and/or sequence of the method as described herein, as performed for example with a VR (virtual reality) headset implementation. The control unit 700 preferably comprises a user interaction interface 702. User interaction interface 702 preferably comprises an automatic chat system, scroll down menu, spoken dialogue interface or any system that enables the user to input information or data.

Control unit 700 also preferably comprises a data collection interface 704, that obtains data from one or more biosensors 706 in order to collect various biosignals, including but not limited to skin temperature, heart rate, respiratory rate, skin galvanic response and every available bodily signals. Data collection interface 704 may be connected to biosensors 706 through a wired or wireless connection.

Each of data collection interface 704 and user interaction interface 702 preferably sends the collected data for storage in one or more databases 708, through a database interface 710. Databases 708 preferably comprise a general database 712 for storing data from a plurality of users. Optionally, data is also copied to an individual database 714 where the data that is stored is the data from one and only one user.

Additionally or alternatively, each of data collection interface 704 and user interaction interface 702 preferably sends the collected data to a manager unit 716. Manager unit 716 uses the data collected to fetch in another structured rules database 718 a protocol determining which data are further needed and, when each type of required data is collected, the manager unit 716 sends a set of commands to a content display controller 720. Content displayer controller 720 uses the commands from manager unit 716 in order to fetch the visual and audio content corresponding directly to the user inputs, as shown in more detail with regard to FIG. 8. This content is then provided to a VR headset 722, for display to the user as performed for example with regard to the method described herein.

Optionally, user interaction interface 702 comprises a chatbot or a spoken dialogue system with the advantage of allowing not only data collection but also interaction between the user and the control unit 700. This allows the data collecting system to be shaped and programmed to gather data but also to interact in a therapeutic manner with the user. For example, optionally user interaction interface 702 delivers therapeutic interventions while collecting data. For example, user interaction interface 702 may provide information to the user, such as motivational information, or may ask questions of the user to provide better therapeutic input during the performance of the method. As another non-limiting example, the therapeutic input could include CBT (cognitive behavioral therapy) dialogue for exercise outside the session or motivational speeches to induce life changes in the user's life.

Various other examples of biosensors 706 may include but are not limited to: ECG system for heart rate monitoring but also in order to determine heart rate variability; body temperature sensor; skin conductance sensor; oxygen saturation sensor; gait sensor; EMG sensor; EEG sensor; gaze tracking; and a galvanic skin response (GSR) sensor. These various biosignals may be used for example to determine emotional arousal.

Figure 8:
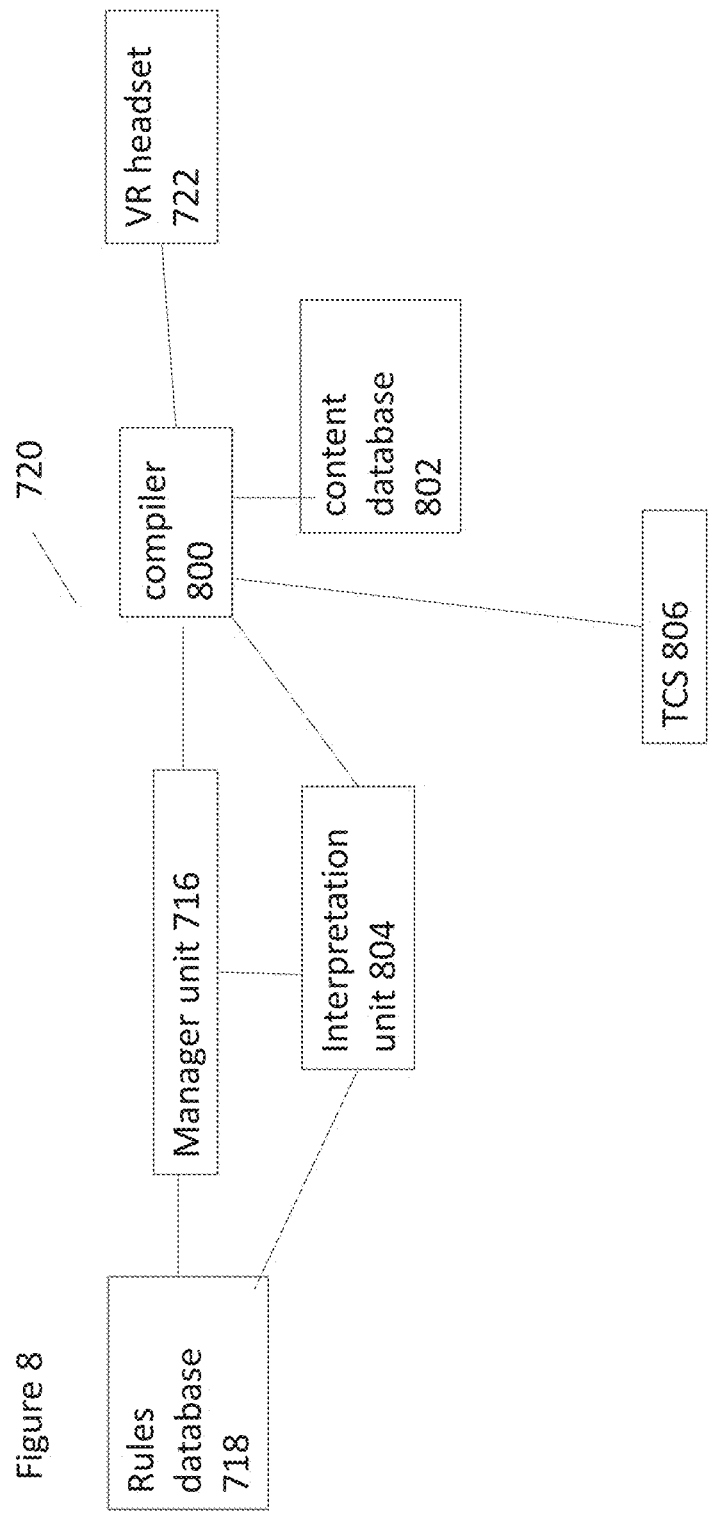
FIG. 8 shows a non-limiting, exemplary implementation of content display controller 720.

FIG. 8 shows a non-limiting, exemplary implementation of content display controller 720. With the exception of manager unit 716, rules database 718 and VR headset 722, which are shown for clarity only, the components shown relate to content display controller 720.

As shown, content display controller 720 comprises a compiler unit 800. Compiler unit 800 uses the commands from manager unit 716 in order to fetch the visual and audio content corresponding directly to the user inputs, for example from a content database 802. To assist manager unit 716 in determining which content is to be obtained, an interpretation unit 804 receives biosignal and/or user interface data from manager unit 716 and analyzes it. Interpretation unit 804 then uses the analyzed data in conjunction with rules database 718, to determine which content would be most useful, and in which sequence. Interpretation unit 804 may use AI (artificial intelligence) or machine learning models. Preferably, manager unit 716 reduces the amount of data to be sent to interpretation unit 804, to reduce the amount of computational resources required.

Next interpretation unit 804 sends this information regarding the content by rendering interpretable commands to the compiler unit 800 for it to be able to fetch the visual and audio content corresponding indirectly to the user inputs and directly to the interpretation output, for example from database 802.

This form of execution has the advantage of delivering specially tailored content to the user either because he directly chose it or because the most well-fitted content was determined from the user input by the interpretation unit 804.

The interpretation unit 804 can be either rule-based or model-based and is built and parameterized by using, interpreting, modeling or by calling to any other form of data treatment in order to process the user's data stored by the data collection unit in the database(s) as described herein.

The (visual) content of the image sequence displayed in the entire VR method is determined directly by the user through one or more commands or input delivered through the user interaction interface, or indirectly through data collected by the data collection interface. In addition, such visual content is preferably determined as described herein through the output of interpretation unit 804 and/or the output of the manager unit 716 sent to the compiler unit 800.

In this implementation shown, the output of the manager unit 716 and the interpretation unit 804 are both provided to compiler unit 800, which in turn then outputs a plurality of commands to VR headset 722.

This has the advantage of tailoring the entire VR method according to the user, their emotions, their expectations and their needs as determined directly by the user or by interpretation of the data collected.

The audio content (spoken presentation) of the VR method is preferably composed of several subparts that are combined by the compiler unit 800 according to the manager unit 716 output (i.e. by the protocol, by the data collected through the user, by the data obtained by interpretation of user input or user bodily signals).

This has the advantage of tailoring the VR method audio according all the variables available from the user and thus corresponding to the user, their emotions, their expectations and their needs as determined directly by the user or by interpretation of the data collected. This also has the advantage to make a wide spectrum of audio generation possible through combinatorial processes.

The light signal included in the initial phase preferably relates to attentional light points being displayed, rather than an actual image. Such a light signal can also be superimposed to any visual or image sequence in the median or final phase, such that it is not limited to the initial phase.

The light signal can also contract or dilate, in terms of the size of the point(s) of light being displayed, in order to guide the user through several exercises including but not limited to breathing exercises, attentional exercises or any method made possible by the movement of the light signal.

This has the advantage to allow cognitive or physical (e.g. breathing) exercises while delivering the VR method.

The light signal can also be superimposed to a black portion of the VR method so to allow what is mentioned above even if the user's eyes are closed. That is, the light signal may be superimposed for a time period during which no image is being shown. This has the advantage to couple cognitive and or physical exercises to the VR method but also to mental imagery exercises.

Variables such as but not limited to body signals (as collected by the above-mentioned sensors) or spoken input can be collected while delivering the VR method and can be used to shape the visual and audio content (light signal, oral presentation) by integrating new content, replace content or change displayed content by modifying variables such as but not limited to shape, luminosity, rhythm, online (i.e. while the VR method is being delivered) so to allow biofeedback techniques, continuous shaping/tailoring of the VR method as well as users guidance through exercises aiming at being aware and/or being able to control body signals.

This has the advantage to make a more active participation of the patient possible while still guiding him towards the therapeutic goals making it a progressive gain of autonomy regarding treatment.

The control unit also allows the generation and/or selection of new content following a request from the user or following interpretation of data requiring the generation of a new content. Generation of new content also includes selection of components of existing content and rearrangement thereof.

The method can be used for physical preparation, physical performance enhancement, self-development, relaxation, meditation, desensitization, exposure techniques, treatment of habit disorders including but not limited to eating disorders, obsessional disorders, addictions, for pain management, phobias, replacement of convenience anesthesia's for any type of interventions, replacement of narcosis for people not allowed to have such an intervention, for adjunct use in interventions that are procedural including but not limited to bandage refection, burn treatment, physical therapy, occupational therapy.

In a form of execution, the VR method as well as the data collection/interaction unit can be used in order to deliver therapies that are biopsychosocial including but not limited to mindfulness-based stress reduction, mindfulness-based cognitive therapy, acceptance and commitment therapy, hypnosis, cognitive behavioral therapy, education.

This has the advantage to follow specific data collection protocols but also starting therapeutic work with the patient while constructing the content of the VR method.

The data collected through the data collection unit can also be used to generate games that are specifically tailored to the patient and to his condition.

This has the advantage to make active participation of the patient as well as other forms of treatment/work possible.

Assessments can be made at the beginning of the VR method and at the end of the VR method.

This has the advantage to assess the efficiency of the form of realization of the VR method so to generate ever improving content for a specific population for a specific user by using the population history order user history.

According to at least some embodiments, FIG. 8 may also feature a transcranial stimulation (TCS) 806, for stimulating the user through any suitable TCS method, such as TDCS (transcranial direct current stimulation), TRNS (transcranial random noise stimulation) and so forth. This addition would permit more responsiveness or effect. The transcranial stimulation would optionally begin as the method began, for example in the initial signal phase. The intensity may optionally decrease slowly, preferably after induction. TCS 806 is controlled with the same controller that is controlling the VR headset 722, for example through compiler 800 as shown. TCS 806 activity may be continuous or periodic. The type of stimulation and its effects would depend on parameters from the user. For example, for situations involving user anxiety, the activity would be used to reduce affect. In other situations, such as for depression, stimulation of the user would result in increased affect, for example to reduce depressive symptoms.

REFERENCE NUMBERS USED IN THE FIGURES

1 virtual reality system
2 display device
3 display screen
3*a* first screen
3*b* second screen
31 first portion of the display screen
32 second portion of the display screen
4 virtual reality module
5 audio playback device
5*a* first transducer
5*b* second transducer
6 sensor module
61 clip
7 control unit
8*a* first virtual object
8*b* second virtual object
9 line of displacement
10 user
11 external module
I1 image sequence
f1 first frequency
f2 second frequency
HR vital parameter
L light signal
O total darkness
S1 first sound signal
S2 second sound signal
S3 third sound signal
S4 fourth sound signal
S5 induction signal
tf final portion
ti initial portion
tm median portion
tn dark portion

What is claimed is:

1. Virtual reality method intended to be implemented in a virtual reality (VR) system, the VR system comprising a VR headset, the method comprising the production of a stimulus in the system during a period of stimulation of a user, the stimulus including:
projecting an image sequence through the VR headset;
producing a plurality of sound signals through the VR headset,
including: a production of a first sound signal including a soundtrack linked to a progression of the image sequence;
a production of a second sound signal having a first frequency and a third sound signal having a second frequency, the second sound signal being audible from one ear and the third sound signal being audible from the other ear of the user;
a production of a fourth sound signal including a spoken presentation;
wherein said period of stimulation is divided into a plurality of portions;
including an induction signal in the stimulus during an initial portion of said period of stimulation; and
during a final portion of said period, decreasing an intensity of the sound signals until reaching a zero intensity, and decreasing an intensity of the image sequence until reaching a zero intensity.

2. The method according to claim 1, said spoken presentation being a discourse of a hypnotic character.

3. The method of claim 1, wherein the VR system further comprises a user interface for receiving user inputs, and a controller for controlling said producing said sound signals and said projecting said image sequence according to said user inputs, such that characteristics of said sound signals and/or of said image sequence are altered according to said user inputs.

4. The method of claim 3, wherein said characteristics of said image sequence comprise one or more of brightness and/or sharpness of the images, and/or content of the images.

5. The method according to claim 3, wherein said VR system further comprises at least one sensor configured for measuring a vital parameter of the user; and including the determination and follow-up of the vital parameter during at least one portion of the period.

6. The method of claim 5, wherein said at least one sensor comprises one or more of ECG (electrocardiogram) system for heart rate monitoring but also in order to determine heart rate variability; body temperature sensor; skin conductance sensor; oxygen saturation sensor; gait sensor; EMG (electromyography) sensor; EEG (electroencephalogram) sensor; gaze tracking and galvanic skin response.

7. The method of claim 5, wherein said VR system further comprises an interpretation unit for interpreting said vital parameter and for outputting commands to said VR headset according to said interpreting.

8. The method of claim 6, wherein said VR system further comprises a data collection interface and a manager unit, the method further comprising collecting biosignals from said at least one sensor by said data collection interface, providing said biosignals by said data collection interface to said manager unit, and selecting one or more biosignals by said manager unit for providing to said interpretation unit.

9. The method of claim 6, wherein said vital parameter of the user includes a cardiac coherence parameter, the method further comprising determining a cardiac coherence threshold; and returning to the initial portion in which the induction signal is generated, when the determined cardiac coherence is below the cardiac coherence threshold.

10. The method of claim 6, adapted for one or more of sports preparation, increasing the physical performance of an athlete, personal development, relaxation, mediation, desensitization to smoking or unhealthy eating habits, preparation for dental and orthopedic operations of short duration, replacing general convenience anesthesias and installing a virtual gastric ring, hypnosis, combination of hypnosis and an EMDR (Eye Movement Desensitization and Reprocessing) type of technique.

11. A virtual reality system, comprising:
a virtual reality device comprising a virtual reality module comprising a display device configured for projecting an image sequence in the visual field of a user; an audio playback device configured for producing a first sound signal including a soundtrack, a second sound signal having a first frequency and audible from one ear of the user, a third sound signal having a second frequency and audible from the other ear of the user, and a fourth sound signal including a spoken presentation;

a plurality of sensors for collecting biosignals from the user;

a data collection unit for receiving said biosignals; and a control unit configured for controlling the virtual reality module, wherein said control unit comprises a manager unit and an interpretation unit, wherein said manager unit receives said biosignals from said data collection interface to said manager unit, wherein said manager unit selects one or more biosignals for providing to said interpretation unit; and wherein said interpretation unit adjusts operation of said virtual reality device according to said biosignals.

12. The system of claim 11, wherein the virtual reality module is configured for projecting a virtual object being displaced between a first and a second area of a display surface of said display device.

13. The system of claim 12, wherein said virtual reality module is configured for generating a two-channel sound simulating a virtual sound source being displaced rhythmically in a to-and-fro movement between a first and a second area of space surrounding the user.

14. The system of claim 11, wherein at least one sensor comprises a sensor for providing a cardiovascular signal; the control unit being adapted so as to be able to determine the cardiac coherence of the user from the cardiovascular signal.

15. The system of claim 11, wherein said at least one sensor comprises one or more of ECG (electrocardiogram) system for heart rate monitoring but also in order to determine heart rate variability; body temperature sensor; skin conductance sensor; oxygen saturation sensor; gait sensor; EMG (electromyography) sensor; EEG (electroencephalogram) sensor; gaze tracking and galvanic skin response.

16. The system of claim 11, further comprising a user interface for receiving user inputs, wherein said controller controls said producing said sound signals and said projecting said image sequence according to said user inputs, such that characteristics of said sound signals and/or of said image sequence are altered according to said user inputs.

17. The system of claim 16, further comprising a TCS (transcranial stimulation) device, wherein said controller controls said TCS according to said user inputs and/or said biosignals.

18. The system of claim 16, further comprising a compiler for receiving said user inputs and/or said biosignals, and for controlling said virtual reality device according to said user inputs and/or said biosignals.

19. The method of claim 1, wherein said VR headset comprises a plurality of display screens, each display screen displaying an image to an eye of the user.

20. The method of claim 19, wherein said VR headset comprises a pair of VR glasses.

* * * * *